(12) United States Patent
Liao et al.

(10) Patent No.: US 8,709,285 B2
(45) Date of Patent: Apr. 29, 2014

(54) IONIC COMPOUND, ANTI-STATIC PRESSURE-SENSITIVE ADHESIVE AND POLARIZER COMPRISING THE SAME

(75) Inventors: Cheng-Chung Liao, Nantou County (TW); Min-Chih Lin, Taoyuan County (TW)

(73) Assignee: BenQ Materials Corporation, Gueishan, Tao-Yuan Hsien (TW)

( * ) Notice: Subject to any disclaimer, the term of this patent is extended or adjusted under 35 U.S.C. 154(b) by 631 days.

(21) Appl. No.: 12/876,172

(22) Filed: Sep. 6, 2010

(65) Prior Publication Data
US 2011/0068306 A1 Mar. 24, 2011

(30) Foreign Application Priority Data
Sep. 23, 2009 (TW) .............................. 98132073 A

(51) Int. Cl.
C09K 19/38 (2006.01)
C09K 19/54 (2006.01)
C09J 133/12 (2006.01)
C09J 133/24 (2006.01)

(52) U.S. Cl.
USPC ........ 252/364; 252/585; 524/105; 548/338.1; 428/1.26; 428/1.54

(58) Field of Classification Search
USPC ............... 252/364, 585; 524/105; 548/338.1; 428/1.26, 1.54
See application file for complete search history.

(56) References Cited

U.S. PATENT DOCUMENTS

| | | | | |
|---|---|---|---|---|
| 3,676,131 A | * | 7/1972 | Willems et al. | 430/434 |
| 3,911,133 A | * | 10/1975 | Edwards | 514/397 |
| 7,622,543 B2 | * | 11/2009 | Tam et al. | 528/271 |
| 8,299,270 B2 | * | 10/2012 | Maruyama | 548/314.4 |
| 2005/0065020 A1 | * | 3/2005 | Holbrey et al. | 502/162 |
| 2007/0252140 A1 | * | 11/2007 | Limmert et al. | 257/40 |
| 2007/0252311 A1 | * | 11/2007 | Tam et al. | 264/477 |
| 2010/0275979 A1 | * | 11/2010 | Maruyama | 136/252 |
| 2012/0046390 A1 | * | 2/2012 | Chen et al. | 523/443 |

* cited by examiner

Primary Examiner — Douglas McGinty
(74) Attorney, Agent, or Firm — Winston Hsu; Scott Margo

(57) ABSTRACT

An ionic compound has the formula (I):

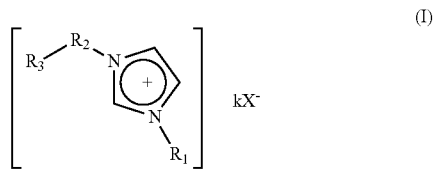

in which, $R_1$ is selected from the group consisting of hydrogen, a $C_1$-$C_{20}$ alkyl, and an aromatic group; $R_2$ is selected from the group consisting of a carbonyl and a $C_1$-$C_{10}$ alkyl; and $R_3$ is selected from the group consisting of an imidazole ring, a $C_1$-$C_{20}$ alkyl, an acrylic group, and an aromatic group; $X^-$ is selected from the group consisting of $Cl^-$, $Br^-$, $I^-$, $NO_3^-$, $AlCl_4^-$, $BF_4^-$, $CF_3SO_3^-$, $(CF_3SO_3)^-$, $CF_3COO^-$, $CH_3COO^-$, and $PF_6^-$; and k is an integer 1 or 2. The ionic compound can be added in a pressure-sensitive adhesive of a polarizer of a liquid crystal display panel to avoid the phenomenon of the static electricity residual when the release film is removed from the pressure-sensitive adhesive.

10 Claims, 1 Drawing Sheet

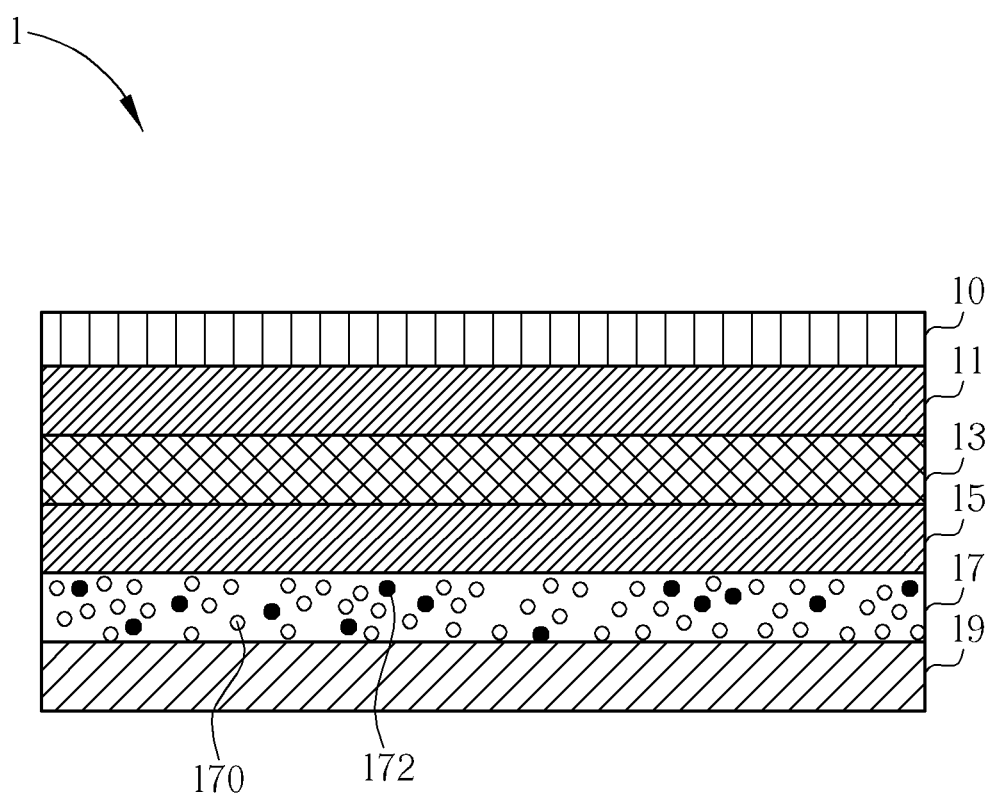

IONIC COMPOUND, ANTI-STATIC PRESSURE-SENSITIVE ADHESIVE AND POLARIZER COMPRISING THE SAME

BACKGROUND OF THE INVENTION

1. Field of the Invention

The present invention relates to an ionic compound, and a pressure-sensitive adhesive and a polarizer both comprising the ionic compound, and particularly to an ionic compound having anti-static effect, and an anti-static pressure-sensitive adhesive and polarizer in which the ionic compound is utilized.

2. Description of the Prior Art

A liquid crystal display (LCD) device generally includes a liquid crystal panel and a polarizer adhered to the Liquid crystal panel through an adhesive layer. The pressure-sensitive adhesive layer is disposed on the outmost surface of the polarizer. A release film is further disposed on the pressure-sensitive adhesive layer for protecting it and the polarizer. Before the adhesion of the polarizer to the liquid crystal panel is carried out, the release film is peeled so as to be removed from the polarizer to expose the pressure-sensitive adhesive layer for the adhesion.

Because the pressure-sensitive adhesive layer and the release film are both made of plastic, static charges may accumulate on the pressure-sensitive adhesive layer upon removal of the release film. When the liquid crystal is subjected to a working voltage under the situation that static charges remain on the pressure-sensitive adhesive layer, the liquid crystal molecules tend to lose alignment ability. This leads to a low yield of the LCD device. Accordingly, it needs an anti-static process for the pressure-sensitive adhesive layer to avoid the aforesaid problem.

For conventional technology, the anti-static process for the pressure-sensitive adhesive layer may include adding an anti-static agent therein or disposing an anti-static layer on the exterior of the polarizer. However, compared with coating an anti-static layer on the exterior of the polarizer, directly adding an anti-static agent in the pressure-sensitive adhesive layer may obtain a better effect.

Currently known anti-static agents include metal powder, fine carbon particulates, ionic liquid or surfactant. For effectively preventing the pressure-sensitive adhesive layer from occurrence of static charges, a great amount of metal powder or fine carbon particulates should be added in the pressure-sensitive adhesive layer. However, the great amount of metal powder or fine carbon particulates will cause the decrease of the transparency of the pressure-sensitive adhesive layer. And that will reduce the brightness of the LCD device. Surfactant tends to migrate to the surface of the pressure-sensitive adhesive layer. And that will deteriorate the adhesion performance of the pressure-sensitive adhesive layer. Also, the surfactant tends to be affected by humidity and then become uncontrollable. Ionic liquid, such as alkali metal salt, or fluoro-organic anion salt, is incompatible with the polymer of the pressure-sensitive adhesive, which will lead to unsuitable anti-static effect for the pressure-sensitive adhesive or defects of physical properties or appearance of the pressure-sensitive adhesive layer.

SUMMARY OF THE INVENTION

Accordingly, one aspect of the present invention is a novel ionic compound, and the ionic compound can be added in a pressure-sensitive adhesive to solve the aforesaid problems.

According to an embodiment, the ionic compound of the present invention has the formula (I) as follows:

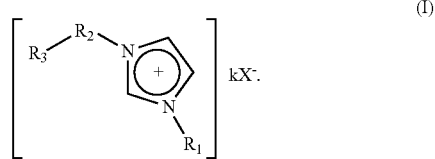

In the formula (I), $R_1$ is selected from the group consisting of hydrogen, a $C_1$-$C_{20}$ alkyl, and an aromatic group; $R_2$ is selected from the group consisting of a carbonyl and a $C_1$-$C_{10}$ alkyl; $R_3$ is selected from the group consisting of an imidazole ring, a $C_1$-$C_{20}$ alkyl, an acrylic group, and an aromatic group; $X^-$ is selected from the group consisting of $Cl^-$, $Br^-$, $I^-$, $NO_3^-$, $AlCl_4^-$, $BF_4^-$, $CF_3SO_3^-$, $(CF_3SO_3)^-$, $CF_3COO^-$, $CH_3COO^-$, and $PF_6^-$; and k is an integer 1 or 2.

Another aspect of the present invention is an anti-static pressure-sensitive adhesive. According to an embodiment, the anti-static pressure-sensitive adhesive includes a polymer and the aforesaid ionic compound incorporated in the polymer. In one embodiment, the ionic compound has the aforesaid formula (I) and description is not repeated herein for concise.

Still another aspect of the present invention is a polarizer. According to an embodiment, the polarizer includes a pressure-sensitive adhesive layer. The pressure-sensitive adhesive layer includes a polymer and the ionic compound having the aforesaid formula incorporated in the polymer. There by, the pressure-sensitive adhesive has a good anti-static effect, adhesion, and exterior integrity. Furthermore, when the polarizer is adhered to a liquid crystal panel, the pressure-sensitive adhesive can provide an excellent adhesive effect and prevent liquid crystal molecules in the liquid crystal panel from being affected by static charges.

These and other objects and purposes of the present invention will no doubt become obvious to those of ordinary skill in the art after reading the following detailed description of the preferred embodiment that is illustrated in the various figures and drawings.

BRIEF DESCRIPTION OF THE DRAWINGS

The FIGURE is a schematic cross-sectional view showing a polarizer according to an embodiment of the present invention.

DETAILED DESCRIPTION

The FIGURE is a schematic cross-sectional view showing a polarizer according to an embodiment of the present invention. As shown in the FIGURE, a polarizer 1 has a multi-layered structure including a protective film 10, a first triacetyl cellulose (TAC) layer 11, a polyvinyl alcohol (PVA) layer 13, a second triacetyl cellulose layer 15, a pressure-sensitive adhesive layer 17 and a release film 19. In an application, a polarizer adheres to a liquid crystal panel (not shown) through the pressure-sensitive adhesive layer 17. The pressure-sensitive adhesive is applied as an entire layer but not pieces in local areas. The location of the pressure-sensitive adhesive in an LCD device should have been well known.

In the embodiment, the pressure-sensitive adhesive layer 17 includes a pressure-sensitive adhesive mainly including a (meth)acrylate-based polymer 170 and an ionic compound 172 incorporated in the polymer. Specifically, the ionic compound 172 has a formula (I) as follows:

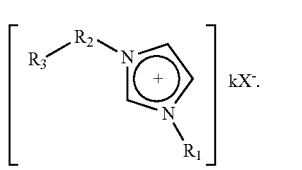

In the formula (I), $R_1$ may be hydrogen, a $C_1$-$C_{20}$ alkyl, or an aromatic group. $R_2$ may be a carbonyl or a carbon chain consisting of n carbons, and n is one selected from positive integers of 1 to 10. $R_3$ may be an imidazole ring, a $C_1$-$C_{20}$ alkyl, an acrylic group, or an aromatic group.

In the formula (I), $X^-$ may be $Cl^-$, $Br^-$, $I^-$, $NO_3^-$, $AlCl_4^-$, $BF_4^-$, $CF_3SO_3^-$, $(CF_3SO_3)^-$, $CF_3COO^-$, $CH_3COO^-$, $PF_6^-$ or other suitable anion. k may be an integer 1 or 2, depending on the charge of the cation in the formula (I).

In one embodiment, $R_3$ may be an imidazole ring. In other words, in a structure of the cation portion of the formula (I), two imidazole rings are connected through a connecting group $R_2$. Thus, the ionic compound of the present invention may have a formula (II) as follows:

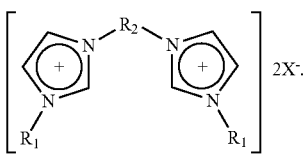

In another embodiment, $R_3$ may include a $C_1$-$C_{20}$ alkyl, an acryloxy group, or an aromatic group. Thus, the ionic compound of the present invention may have a formula (III) as follows:

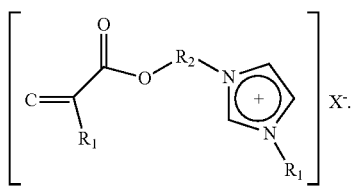

In the formulas (II) and (III), $X^-$ may be $Cl^-$, $Br^-$, $I^-$, $NO_3^-$, $AlCl_4^-$, $BF_4^-$, $CF_3SO_3^-$, $(CF_3SO_3)^-$, $CF_3COO^-$, $CH_3COO^-$, $PF_6^-$ or other suitable anion.

Furthermore, since R2 in the formula (I) may be a carbonyl or a carbon chain consisting of n carbons, the ionic compound of the present invention may have a formula (IV) or (V) derived from the formula (II).

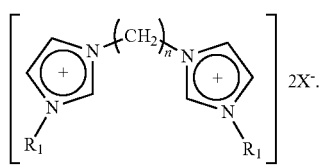

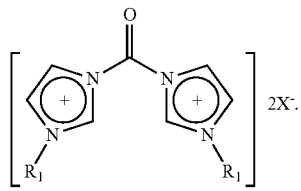

Furthermore, the ionic compound of the present invention may have a formula (VI) derived from the formula (III), wherein, m is an integer of from 1 to 20.

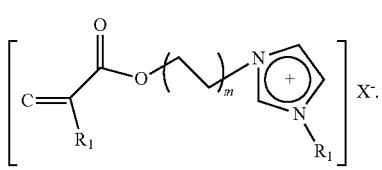

Specifically, when the ionic compound of the present invention has a structure of the formula (IV), the chain length decides the state of the ionic compound. When the chain length increases, that is, n tends toward 10, the ionic compound tends to be in a liquid state. In the other hand, when the chain length decreases, that is, n tends toward 1, the ionic compound tends to be in a solid state. For example, when the carbon number n of the carbon chain is 2, the ionic compound is in a solid state, and when the carbon number n of the carbon chain is 8, the ionic compound is in a liquid state.

Compared with the solid ionic compound, the liquid ionic compound diffuses and dissolves in the polymer more easily. However, purification of the ionic compound in a liquid state is not easy as compared with the ionic compound in a solid state. Accordingly, in an application, the carbon number of the carbon chain of the connecting group of the ionic compound may be varied as desired by users or designers.

It should be noted that the structures of formulas (I), (II), (III), (IV), (V) and (VI) are just for illustrating the structure of the ionic compound of the present invention and should not to be construed as the limitation of the present invention.

In one embodiment, the pressure-sensitive adhesive of the present invention may include a (meth)acrylic group-based polymer and the polymer may include a monomeric unit based on an alkyl (meth)acrylate monomer, in which the alkyl has a carbon number of 1 to 12. Such kind of (meth)acrylic group-based polymer is well compatible with the aforesaid ionic compound. For example, the aforesaid (meth)acrylate may be methyl (meth)acrylate, ethyl (meth)acrylate, n-butyl (meth)acrylate, sec-butyl (meth)acrylate, tert-butyl (meth)acrylate, isobutyl (meth)acrylate, hexyl (meth)acrylate, 2-ethylhexyl (meth)acrylate, n-octyl (meth)acrylate, isooctyl (meth)acrylate, n-nonyl (meth)acrylate, isononyl (meth)acrylate, n-decyl (meth)acrylate, isodecyl (meth)acrylate, n-dodecyl (meth)acrylate, or the like.

Preferably, the polymer may include a monomeric unit based on an alkyl (meth)acrylate monomer, in which the alkyl has a carbon number of 2 to 8. For example, the aforesaid (meth)acrylate may be n-butyl (meth)acrylate, sec-butyl (meth)acrylate, tert-butyl (meth)acrylate, isobutyl (meth)acrylate, hexyl (meth)acrylate, 2-ethylhexyl (meth)acrylate, n-octyl (meth)acrylate, isooctyl (meth)acrylate, n-nonyl (meth)acrylate, isononyl (meth)acrylate, n-decyl (meth)acrylate, isodecyl (meth)acrylate, or the like.

It should be noted that the (meth)acrylate as the aforesaid can be utilized singly or in combination to serve as a monomer or monomers in the pressure-sensitive adhesive, without the limitation in the present invention. Furthermore, in an application, the monomer for the polymer can be polymerized by solution polymerization, photo-polymerization, bulk polymerization, emulsion polymerization, suspension polymerization, or other type of polymerization.

The viscoelasticity of the pressure-sensitive adhesive depends on the weight average molecular weight of the polymer. Generally, suitable weight average molecular weight of the polymer for the pressure-sensitive adhesive may be from 100,000 to 5,000,000, preferably 200,000 to 4,000,000, and more preferably 300,000 to 3,000,000. If the weight average molecular weight of the polymer is less than 100,000, the cohesive strength of the pressure-sensitive adhesive will be so low that residual paste is easily produced. In the other hand, if the weight average molecular weight of the polymer is greater than 5,000,000, the cohesive strength of the pressure-sensitive adhesive will be so high that the flowability of the pressure-sensitive adhesive will be low and the wetting of the polarizer will be insufficient, and, that will make the pressure-sensitive adhesive layer to tend to be peeled off the polarizer. Accordingly, too less and too more weight average molecular weight of the polymer both cause defects in the pressure-sensitive adhesive, and it is disadvantageous to the yield of the LCD device.

Furthermore, the glass transition temperature of the aforesaid polymer can be adjusted by altering the amount ratio of the (meth)acrylate-based monomeric unit and other components. Generally, the suitable glass transition temperature of the polymer for the pressure-sensitive adhesive is higher than −100° C., preferably from −90° C. to 0° C., and more preferably from −80° C. to −10° C. If the glass transition temperature of the polymer is higher than 0° C., the flowability of the pressure-sensitive adhesive will be low and the wetting of the polarizer will be insufficient, and, in turn, the pressure-sensitive adhesive layer will tend to be peeled off the polarizer.

Furthermore, according to another embodiment, the pressure-sensitive adhesive may further include a crosslinking agent to crosslink the polymer in the pressure-sensitive adhesive, and that will improve heat resistance of the pressure-sensitive adhesive. In an application, the crosslinking agent may be for example isocyanate compound, epoxy compound, melamine-based resin or azacyclopropane compound, but not limited thereto.

In conclusion, the pressure-sensitive adhesive of the polarizer of the present invention for LCD device may include the aforesaid ionic compound and a (meth)acrylic group-based polymer.

The Synthesis of the pressure-sensitive adhesive of the present invention is described specifically as follows.

Example 1-1

Preparation of Acrylic Polymer

A monomer mixture of 94.7 parts by weight of n-butyl acrylate, 5 parts by weight of acrylic acid, and 0.3 parts by weight of hydroxyethyl methacrylate was placed in a 0.5 L reactor equipped with nitrogen, refluxing, and cooling systems, and further added by 150 parts by weight of ethyl acetate as a solvent. Thereafter, nitrogen purged for 20 minutes, and 0.03 parts by weight of azobisisobutyronitrile as an initiator was then added. The above mixture was subjected to a polymerization at 60° C. for about 8 hours, to give the title polymer.

Example 1-2

Synthesis of Ionic Compounds Having the Formula (V)

6 grams of N,N'-carbonyldiimidazole was placed in a mononecked flask and then about 20 ml of dichloromethane was added. A filling funnel was set on the mononecked flask, and 10 ml of methyl trifluoromethanesulfonate was taken with a glass syringe needle in a hood and injected into the filling funnel under isolation from the atmosphere and moisture, to avoid hydrolysis of methyl trifluoromethanesulfonate with water. Methyl trifluoromethanesulfonate in the filling funnel was slowly added into the mononecked flask under 0-10° C. ice-water bath and allowed to react for about 3 hours, resulting in white salt precipitates. The white salt was filtered and washed using a small amount of dichloromethane to remove excess methyl trifluoromethanesulfonate. The washing and filtration were repeated until the filtrate was colorless. Thereafter, the obtained salt was placed in a mononecked flask to remove residual dichloromethane by rotary concentration, and then vacuum-dried.

6 grams of N,N'-carbonyldiimidazole was placed in a mononecked flask and then about 20 ml of dichloromethane was added. A filling funnel was set on the mononecked flask, and 10.5 ml of ethyl trifluoromethanesulfonate was taken with a glass syringe needle in a hood and injected into the filling funnel under isolation from the atmosphere and moisture, to avoid hydrolysis of ethyl trifluoromethanesulfonate with water. Ethyl trifluoromethanesulfonate in the filling funnel was slowly added into the mononecked flask under 0-10° C. ice-water bath and allowed to react for about 3 hours, resulting in white salt precipitates. The white salt was filtered and washed using a small amount of dichloromethane to remove excess ethyl trifluoromethanesulfonate. The washing and filtration were repeated until the filtrate was colorless. Thereafter, the obtained salt was placed in a mononecked flask to remove residual dichloromethane by rotary concentration, and then vacuum-dried.

Example 1-3

Synthesis of Ionic Compounds Having the Formula (VI)

0.3 mole (39.04 grams) of 2-hydroxyethyl methacrylate (M.W.=130.14) was placed in a mononecked flask. A filling funnel was set on the mononecked flask, and 22 ml of thionyl chloride (somewhat excess, d=1.638, M.W.=118.17) was taken with a glass syringe needle in a hood to be allowed to react with 2-hydroxyethyl methacrylate. The gasses, such as sulfur dioxide and hydrochloric acid, produced during the reaction, might be introduced into water through a plastic conduit. After the reaction was carried out for one day, the resultant products were placed into a separatory funnel, and 10 ml of dichloromethane and 500 ml of 1M potassium hydroxide solution were added. After extraction by the separatory funnel, the lower organic layer was collected. The remaining aqueous layer including the potassium hydroxide solution was added with 5 ml of dichloromethane each time and the above steps were repeated twice. All of the organic layers were combined and dehydrated by adding anhydrous magnesium sulfate. After the magnesium sulfate was filtered off, the organic layer was stored for use.

28.8 grams of N-methylimidazole was placed in a mononecked flask and then the aforesaid organic layer was added. The mononecked flask was equipped with a condenser and the reaction temperature was controlled in the range of from 60 to 70° C. The reaction was allowed to last for one day. Thereafter, the produced salt was filtered, and un-reacted N-methylimidazole was rinsed off using dichloromethane. The filtration and the rinsing were repeated until the obtained salt was white and the filtrate was colorless. Thereafter, the obtained salt was placed in a mononecked flask to remove residual dichloromethane by rotary concentration.

Finally, 5 grams of the above-obtained compound was placed in a conical flask and 10 grams of water was added. 5 grams of $(CF_3C_3O_2)_2NLi$ was further added. The mixture was fast stirred at room temperature for about one hour, resulting in a water-insoluble white salt. The white salt is filtered, rinsed by a small amount of water, and vacuum-dried for use.

Example 1-4

Preparation of the Pressure-Sensitive Adhesives of the Present Invention 100 parts by weight of acrylic polymer prepared in Example 1-1 was added with 0.4 parts by weight of trihydroxymethyl propane toluene diisocyanate adduct, 0.8 parts by weight of aluminum acetylacetonate, and 0.04 parts by weight of [3-(2,3-epoxypropoxy)propyl]trimethylsilane. Thereafter, the ionic compound prepared in Example 1-2 or Example 1-3 was added in various ratios according to Table 1.

TABLE 1

| | ionic compound/parts by weight | | |
|---|---|---|---|
| No. | A1 | A2-1 | A2-2 |
| 1 | 0.1 | 0 | 0 |
| 2 | 0.5 | 0 | 0 |
| 3 | 1 | 0 | 0 |
| 4 | 5 | 0 | 0 |
| 5 | 0 | 0.1 | 0 |
| 6 | 0 | 0.5 | 0 |
| 7 | 0 | 1 | 0 |
| 8 | 0 | 5 | 0 |
| 9 | 0 | 0 | 0.1 |
| 10 | 0 | 0 | 0.5 |
| 11 | 0 | 0 | 1 |
| 12 | 0 | 0 | 5 |

*A1 represents the formula (VI) wherein $R_1$ is $CH_3$.
*A2-1 represents the formula (V) wherein $R_1$ is Me.
*A2-2 represents the formula (V) wherein $R_1$ is Et.

The properties such as surface resistance, haze value, and holding power of 12 pressure-sensitive adhesives prepared in Example 1-4 will be compared as follows. The test results are shown in Table 2.

Example 1-5

Test for Surface Resistance of the Pressure-Sensitive Adhesive

In this example, surface resistance of the aforesaid pressure-sensitive adhesives was determined by utilizing a device (Model: Mitsubishi Chemical Corporation Hiresta-Up Mcp-HT450) applied with an external voltage of 10 to 1,000 volts. When a surface resistance is determined to be higher than $10^{13} \Omega/\square$ at 27.6° C. under a relative humidity of 46% and application of 500 volts, the pressure-sensitive adhesive is evaluated as not having anti-static properties.

Example 1-6

Test for Haze Properties of the Pressure-Sensitive Adhesive

The haze value was determined in accordance with the method specified in ASTM D1003-95 and JIS K7105. A diffusion light transmittance (Td) and a total light transmittance (Ti) were determined using an all-in-one light-transmittance detector, and the haze value was defined as the percentage of Td to Ti. The pressure-sensitive adhesive to be tested was applied onto a test sheet, and the haze value and the light transmittance were directly determined by a haze value meter. A background value was further deducted from the determined value.

Example 1-7

Tensile Test for the Pressure-Sensitive Adhesive

In this example, the tensile properties of the aforesaid pressure-sensitive adhesive were determined by a tensile tester (Model: Dachang, QC-508PC, fabricated by Cometech Testing Machines Co., Ltd, Taiwan). The pressure-sensitive adhesive sheet was cut into a strip-shaped specimen with a width of 2.5 cm. After the release film was removed, the specimen was placed to stick on SBS316 standard stainless steel plate and heavily rolled by a roller for 10 minutes. The specimen was then tested for peeling force (180 degrees) at a drawing rate of 30 mm/min by a tensile tester.

Example 1-8

Holding Power Test for the Pressure-Sensitive Adhesive

In this example, the pressure-sensitive adhesive sheet was cut into a strip-shaped specimen with a width of 2.5 cm. The specimen was placed to stick on SBS316 standard stainless steel plate and heavily pressed by a roller for 10 minutes. Only a specimen with a size of 2.5 cm×2.5 cm was kept and placed into an oven at 70° C. for 20 minutes and then a 1-kilogram weight was hung from the pressure-sensitive adhesive specimen. The moving distance is observed after 40 minutes.

TABLE 2

| No. | Surface resistance ($\Omega/\square$) | Haze Value | Tensile strength (gf/25 mm) | Holding power (mm) |
|---|---|---|---|---|
| 1 | $9.02 \times 10^{11}$ | 0.1 | 524 | 0 |
| 2 | $5.07 \times 10^{11}$ | 0.1 | 472 | 0 |
| 3 | $4.62 \times 10^{11}$ | 0.1 | 419 | 0 |
| 4 | $3.60 \times 10^{11}$ | 0.1 | 266 | 0 |
| 5 | $1.09 \times 10^{12}$ | 0.1 | 618 | 0 |
| 6 | $2.46 \times 10^{12}$ | 0.1 | 450 | 0 |
| 7 | $7.74 \times 10^{11}$ | 0.1 | 312 | 0 |
| 8 | $5.90 \times 10^{10}$ | 0.1 | 240 | 0 |
| 9 | $1.41 \times 10^{12}$ | 0.1 | 658 | 0 |
| 10 | $3.01 \times 10^{12}$ | 0.1 | 571 | 0 |
| 11 | $2.10 \times 10^{11}$ | 0.1 | 453 | 0 |
| 12 | $6.92 \times 10^{10}$ | 0.1 | 289 | 0 |

As shown in Table 2, the resistance and the tensile strength substantially decrease as the addition amount of the ionic compound increases. And, each holding power is zero. The aforesaid example indicates that the pressure-sensitive adhesive of the present invention has a good adhesion and anti-static effect. Furthermore, the resistance of the pressure-sensitive adhesive of the present invention can be greatly reduced to provide a good anti-static effect as long as a little amount of the ionic compound of the present invention is added. Furthermore, as shown in Table 2, the appearance of all the tested pressure-sensitive adhesive sheets is clear and accordingly the brightness of the LCD device will not be affected.

The synthesis of another embodiment of the pressure-sensitive adhesive of the present invention is described as follows.

Example 2-1

Synthesis of 1,1'-di(methyl)-3,3'-ethylenediimidazolium di((bis-trifluoromethylsulfonyl)imide) (Which Represents the Formula (IV) Wherein $R_1$ is $CH_3$ and n is 2.)

First, 22.4 parts by weight of 1-methylimidazole liquid was placed in a reactor under nitrogen atmosphere and added by 120 parts by weight of acetonitrile. Next, 25.6 parts by weight of 1,2-dibromoethane liquid was gradually added under stirring. The liquid mixture was continuously stirred in an oil bath at 67° C. for 24 hours, and then cooled to room temperature. Thereafter, acetonitrile in the mixture was removed by rotary evaporation. The remaining liquid was extracted repeatedly by deionized water and ethyl acetate, and the aqueous layers were collected, concentrated by rotary evaporation, and dried using a vacuum oven, to give a precursor.

10 parts by weight of the aforesaid precursor was added into 40 ml of deionized water in a reactor, and then an aqueous solution of 17 parts by weight of lithium bis(trifluoromethane-sulfonyl)imide dissolved in 20 parts by weight of deionized water was slowly added into the reactor. The resulting mixture was stirred at room temperature for 1 hour and filtered to obtain a white solid. The white solid was washed repeatedly with deionized water and ethanol to obtain a solid 1,1'-di(methyl)-3,3'-ethylenediimidazolium di((bis-trifluoromethylsulfonyl)imide).

Example 2-2

Synthesis of 1,1'-di(methyl)-3,3'-octylenediimidazolium di((bis-trifluoromethylsulfonyl)imide) (Which Represents the Formula (IV) Wherein $R_1$ is $CH_3$ and n is 8.)

The ionic compounds of the present invention having various chemical structures can be synthesized by changing the formula of the precursor described in Example 2-1. In this example, 22.4 parts by weight of 1-methylimidazole liquid and 20 parts by weight of 1,8-dibromooctane liquid were utilized. The oil bath was at 70° C. Furthermore, 9.66 parts by weight of the precursor was added into 30 ml of deionized water, and an aqueous solution of 12.8 parts by weight of lithium bis(trifluoromethane-sulfonyl)imide dissolved in 10 parts by weight of deionized water was utilized. By the aforesaid steps, 1,1'-di(methyl)-3,3'-octylenediimidazolium di((bis-trifluoromethylsulfonyl)imide) was obtained.

Example 2-3

Synthesis of the Pressure-Sensitive Adhesive Sheet of the Present Invention

Example 2-3-1

100 parts by weight of the acrylic polymer obtained in Example 1-1 was added with 0.4 parts by weight of trihydroxymethyl propane toluene diisocyanate adduct (made by Rhodia company), 0.8 parts by weight of aluminum acetylacetonate, and 0.04 parts by weight of [3-(2,3-epoxypropoxy)propyl]trimethylsilane as crosslinking agents and additives. The aforesaid compounds were mixed and stirred at room temperature for 5 minutes, obtaining a (meth)acrylic pressure-sensitive adhesive solution. This (meth)acrylic pressure-sensitive adhesive solution was applied on to a test plate to form a pressure-sensitive adhesive layer, and it was baked and cured at room temperature, obtaining a pressure-sensitive adhesive sheet.

Example 2-3-2

In addition to the compounds (the acrylic polymer, crosslinking agents, additives) used in Example 2-3-1, 5 ml (0.02 parts by weight) of 1,1'-di(methyl)-3,3'-ethylenediimidazolium di((bis-trifluoromethylsulfonyl)imide) was further added in the compounds and mixed, for preparing the pressure-sensitive adhesive solution. The other steps for preparing the pressure-sensitive adhesive sheet were the same as Example 2-3-1 and accordingly not repeatedly described herein.

Example 2-3-3

5 ml (0.02 parts by weight) of 1,1'-di(methyl)-3,3'-ethylenediimidazolium di((bis-trifluoromethylsulfonyl)imide) as utilized in Example 2-3-2 was replaced with 5 ml (0.1 parts by weight) of 1,1'-di(methyl)-3,3'-ethylenediimidazolium di((bis-trifluoromethylsulfonyl)imide).

Example 2-3-4

5 ml (0.02 parts by weight) of 1,1'-di(methyl)-3,3'-ethylenediimidazolium di((bis-trifluoromethylsulfonyl)imide) as utilized in Example 2-3-2 was replaced with 5 ml (0.2 parts by weight) of 1,1'-di(methyl)-3,3'-ethylenediimidazolium di((bis-trifluoromethylsulfonyl)imide).

Example 2-3-5

5 ml (0.02 parts by weight) of 1,1'-di(methyl)-3,3'-ethylenediimidazolium di((bis-trifluoromethylsulfonyl)imide) as utilized in Example 2-3-2 was replaced with 5 ml (0.02 parts by weight) of 1,1'-di(methyl)-3,3'-octylenediimidazolium di((bis-trifluoromethylsulfonyl)imide).

Example 2-4

Properties Test for Pressure-Sensitive Adhesive Sheet

The surface resistance, tensile strength, and holding power of the pressure-sensitive adhesive sheets prepared in Example 2-3 were determined in accordance with Examples 1-5 to 1-8. The results are shown in Table 3.

TABLE 3

| | Surface resistance (Ω/□) | Tensile strength (gf/25 mm) | Holding power (mm) | Appearance |
|---|---|---|---|---|
| Ex. 2-3-1 | >$10^{14}$ | 573 | 0 | Clear |
| Ex 2-3-2 | $6.76 \times 10^{11}$ | 561 | 0 | Clear |
| Ex 2-3-3 | $6.04 \times 10^{11}$ | 538 | 0 | Clear |
| Ex 2-3-4 | $5.25 \times 10^{11}$ | 488 | 0 | Clear |
| Ex 2-3-5 | $3.70 \times 10^{11}$ | 585 | 0 | Clear |

As shown in Table 3, the resistance and the tensile strength of the pressure-sensitive adhesive sheet decrease as the addition amount of 1,1'-di(methyl)-3,3'-ethylenediimidazolium di((bis-trifluoromethylsulfonyl)imide) increases. And, each holding power is zero. The aforesaid examples indicate that the pressure-sensitive adhesive of the present invention has a good adhesion and anti-static effect. Please note that in Examples 2-3-2 and 2-3-5, the resistance of the pressure-sensitive adhesive can be greatly reduced to provide a good anti-static effect by adding just a little amount of 1,1'-di(methyl)-3,3'-ethylenediimidazolium di((bis-trifluoromethylsulfonyl)imide) or 1,1'-di(methyl)-3,3'-octylenediimidazolium di((bis-trifluoromethylsulfonyl)imide). Furthermore, as shown in Table 3, the appearance of all the tested pressure-sensitive adhesive sheets is clear and accordingly the brightness of the LCD device will not be affected.

Compared with prior art, the pressure-sensitive adhesive of the present invention includes an ionic compound having one or two imidazole rings and a (meth)acrylic group-based polymer. Furthermore, the ionic compound of the present invention may further include anion and be ion-changeable with the cation having the imidazole ring, to allow the ionic compound of the present invention to turn the hydrophilicity into the hydrophobicity. Therefore, the pressure-sensitive adhesive of the present invention has good anti-static properties, adhesion performance, and clarity, for suitably being utilized to attach a polarizer on a liquid crystal panel. Furthermore, because the ionic compound of the present invention is easily uniformly diffused into the polymer without incompactibility issue, flaws or defects for physical properties or appearance of the pressure-sensitive adhesive to cause a low yield of LCD device can be avoided.

Those skilled in the art will readily observe that numerous modifications and alterations of the device and method may be made while retaining the teachings of the invention.

What is claimed is:

1. An anti-static pressure-sensitive adhesive comprising:
an acrylic polymer comprising a monomeric unit based on an alkyl (meth)acrylate, wherein the alkyl has a carbon number of 1 to 12;
a crosslinking agent to crosslink the acrylic polymer; and
an ionic compound incorporated in the acrylic polymer, wherein the ionic compound has the formula (IV):

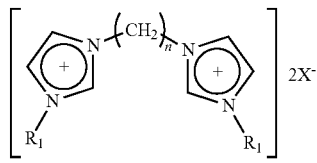

(IV)

wherein, $R_1$ is selected from the group consisting of hydrogen, a $C_1$-$C_{20}$ alkyl, and an aromatic group;
$X^-$ is selected from the group consisting of $Cl^-$, $Br^-$, $I^-$, $NO_3^-$, $AlCl_4^-$, $BF_4^-$, $CF_3SO_3^-$, $CF_3COO^-$, $CH_3COO^-$, and $PF_6^-$; and
n is an integer 1 to 10.

2. The anti-static pressure-sensitive adhesive according to claim 1, wherein n is 2 or less than 2, and the ionic compound is in a solid state.

3. The anti-static pressure-sensitive adhesive according to claim 1, wherein n is 8 or greater than 8, and the ionic compound is in a liquid state.

4. The anti-static pressure-sensitive adhesive according to claim 1, wherein the acrylic polymer comprises a monomeric unit based on an alkyl (meth)acrylate, and the alkyl has a carbon number of 2 to 8.

5. The anti-static pressure-sensitive adhesive according to claim 1, wherein the acrylic polymer has a weight average molecular weight of 100,000 to 5,000,000.

6. The anti-static pressure-sensitive adhesive according to claim 1, wherein the acrylic polymer has a glass transition temperature of 100° C. to 0° C.

7. A polarizer, comprising:
a pressure-sensitive adhesive layer comprising an acrylic polymer and an ionic compound incorporated in the acrylic polymer, wherein the ionic compound has the formula (IV):

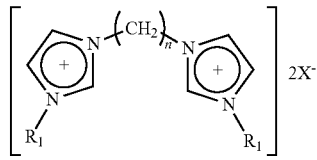

(IV)

wherein $R_1$ is selected from the group consisting of hydrogen, a $C_1$-$C_{20}$ alkyl, and an aromatic group;
$X^-$ is selected from the group consisting of $Cl^-$, $Br^-$, $I^-$, $NO_3^-$, $AlCl_4^-$, $BF_4^-$, $CF_3SO_3^-$, $CF_3COO^-$, $CH_3COO^-$, and $PF_6^-$; and
N is an integer 1 to 10.

8. The polarizer according to claim 7, wherein n is 2 or less than 2, and the ionic compound is in a solid state.

9. The polarizer according to claim 7, wherein n is 8 or greater than 8, and the ionic compound is in a liquid state.

10. The polarizer according to claim 7, wherein, the acrylic polymer comprises a monomeric unit based on an alkyl (meth)acrylate, and the alkyl has a carbon number of 2 to 8.

* * * * *